(12) United States Patent
Akpinar (10) Patent No.: US 10,905,406 B2
(45) Date of Patent: Feb. 2, 2021

(54) MEDICAL IMPLANTABLE OCCLUSION DEVICE, AND METHOD FOR IMPLANTATION THEREOF

(71) Applicant: Occlutech Holding AG, Schaffhausen (CH)

(72) Inventor: Mehmet Hakan Akpinar, Istanbul (TR)

(73) Assignee: Occlutech Holding AG, Schaffhausen (CH)

( * ) Notice: Subject to any disclaimer, the term of this patent is extended or adjusted under 35 U.S.C. 154(b) by 214 days.

(21) Appl. No.: 15/872,908

(22) Filed: Jan. 16, 2018

(65) Prior Publication Data

US 2018/0153533 A1   Jun. 7, 2018

Related U.S. Application Data (63) Continuation of application No. 15/174,948, filed on Jun. 6, 2016, now Pat. No. 9,901,330, which is a continuation of application No. 14/241,062, filed as application No. PCT/EP2012/068760 on Sep. 24, 2012, now Pat. No. 9,375,209.

(Continued)

(30) Foreign Application Priority Data

Sep. 22, 2011 (EP) .................... 11182390

(51) Int. Cl.
*A61B 17/00* (2006.01)
*A61B 17/12* (2006.01)
*A61F 2/24* (2006.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC ................ A61B 17/12; A61B 17/0057; A61B 17/12122; A61B 17/12172;
(Continued)

(56) References Cited

U.S. PATENT DOCUMENTS

| | | |
|---|---|---|
| 5,486,193 A | 1/1996 | Bourne et al. |
| 5,879,366 A | 3/1999 | Shaw et al. |

(Continued)

FOREIGN PATENT DOCUMENTS

| | | |
|---|---|---|
| EP | 1982655 A1 | 10/2008 |
| WO | WO1999/039646 A1 | 8/1999 |

(Continued)

OTHER PUBLICATIONS

United States Patent and Trademark Office, Notice of Allowance dated Feb. 29, 2016 in U.S. Appl. No. 14/241,062, 12 pages.
(Continued)

*Primary Examiner* — Vi X Nguyen
(74) *Attorney, Agent, or Firm* — Inskeep IP Group, Inc.

(57) ABSTRACT

A medical occlusion device with proximal and distal portions separated by a connecting member. The proximal and distal portions are shaped to reduce the occurrence of paravalvular leakage by including a peripheral edge that is characterized by rounded corners.

19 Claims, 10 Drawing Sheets

Related U.S. Application Data (60) Provisional application No. 61/537,623, filed on Sep. 22, 2011.

(52) U.S. Cl.
CPC ...... *A61B 17/12172* (2013.01); *A61F 2/2409* (2013.01); *A61B 2017/00243* (2013.01); *A61B 2017/00592* (2013.01); *A61B 2017/00606* (2013.01); *A61B 2017/12004* (2013.01)

(58) Field of Classification Search
CPC .... A61B 17/12031; A61B 2017/00592; A61B 2017/00637; A61B 2017/00654; A61B 17/00; A61B 17/08
See application file for complete search history.

(56) References Cited

U.S. PATENT DOCUMENTS

| | | |
|---|---|---|
| 6,712,836 B1 | 3/2004 | Berg et al. |
| 2005/0267524 A1 | 12/2005 | Chanduszko |
| 2005/0267525 A1 | 12/2005 | Chanduszko |
| 2006/0241690 A1* | 10/2006 | Amplatz ............ A61B 17/0057 606/213 |
| 2007/0265656 A1 | 11/2007 | Amplatz et al. |

FOREIGN PATENT DOCUMENTS

| | | |
|---|---|---|
| WO | WO2008/071952 A2 | 6/2008 |
| WO | WO2008/153872 A2 | 12/2008 |

OTHER PUBLICATIONS

WIPO, European International Preliminary Examining Authority, International Preliminary Report on Patentability dated Dec. 20, 2013 in International Patent Application No. PCT/EP2012/068760, 11 pages.

WIPO, European International Search Authority, International Search Report dated Dec. 20, 2012 in International Patent Application No. PCT/EP2012/068760, 7 pages.

\* cited by examiner

Prior art

MEDICAL IMPLANTABLE OCCLUSION DEVICE, AND METHOD FOR IMPLANTATION THEREOF

RELATED APPLICATIONS

This application is a continuation of U.S. patent application Ser. No. 15/174,948 filed Jun. 6, 2016 entitled Medical Implantable Occlusion Device, And Method For Implantation Thereof, which a continuation of U.S. patent application Ser. No. 14/241,062 filed Feb. 25, 2014 entitled Medical Implantable Occlusion Device, And Method For Implantation Thereof (now U.S. Pat. No. 9,375,209 issued Jun. 28, 2016), which is the U.S. National Phase of and claims priority to International Patent Application No. PCT/EP2012/068760, International Filing Date Sep. 24, 2012, entitled Medical Implantable Occlusion Device, And Method For Implantation Thereof, which claims benefit of U.S. Provisional Application Ser. No. 61/537,623, filed Sep. 22, 2011 entitled Medical Implantable Occlusion Device, And Method For Implantation Thereof; and European Application No. 11182390.2, filed Sep. 22, 2011 entitled Medical Implantable Occlusion Device; all of which are incorporated herein by reference in their entireties.

FIELD OF THE INVENTION

This invention pertains in general to the field of medical implants. More particularly the invention relates to an intraluminally deliverable occlusion device for selective occlusion of a target site in a body lumen, such as the body's circulatory system, and more particularly for occlusion of paravalvular leaks, and method for implantation of such occlusion device.

BACKGROUND OF THE INVENTION

Various intravascular deliverable devices are used for treating specific conditions via access through body lumina, such as patient's circulatory system. The target site may for instance be an atrial or ventricular septum having a defective opening to be occluded, such as devices for treating septal defects and the like. In certain circumstances, it may be necessary to occlude a patient's lumen, vessel, chamber, channel, hole, or cavity such as to stop blood flow there through. One such condition known in the art is Para-Valvular Leak (PVL) which may occur in association with surgical implantation of prosthetic valves in the heart, and with interventional valve implantations in general, i.e. transcatheter aortic valve intervention (TAVI). When the prosthetic valve is fixed by sutures micro-holes are created where the sutures penetrate the tissue. These micro-holes can become dilated over time and grow larger and also merge together, thereby creating undesired blood passages around the valve compromising the normal flow of blood through the valve. Any surgical procedure around the valve may create such undesired leaks. Whether it is implantation of a prosthetic valve or procedures around the native heart valve, sutures or other means that must penetrate the surrounding tissue may be the source of such leaks. Leaks around the valve may also arise because of other undesired conditions. For example, after the replacement of the valve the pressure increases which could cause damages on the degenerated tissue around the valve area, such that leaks occur. That tissue can also be perforated with guide wires or guiding catheters during any other heart surgery procedure, with leaks as a consequence.

In the case of prosthetic valves, over 210.000 valve replacements are performed each year world wide. In between 3-12% of the operations there is paravalvular leakage, and 3-4% is critical and needs reoperation. The diagnosis of paravalvular leak is done during the first year of the implantation. The patient may have a small PVL that may not effect the blood transfusion but can be diagnosed with imaging techniques such as TEE. Usually surgical therapy is the standard for treating paravalvular leaks but reoperation increases mortality and morbidity as compared to the first operation, i.e. reoperation is more difficult and increases the risk factor. After surgical reoperations 20% of the patients has residual or recurrent paravalvular leak. Another possibility is to use medical therapy, which is palative, i.e. the symptoms can be decreased but hemodynamic anomalies can not be regulated.

Figure 1A:
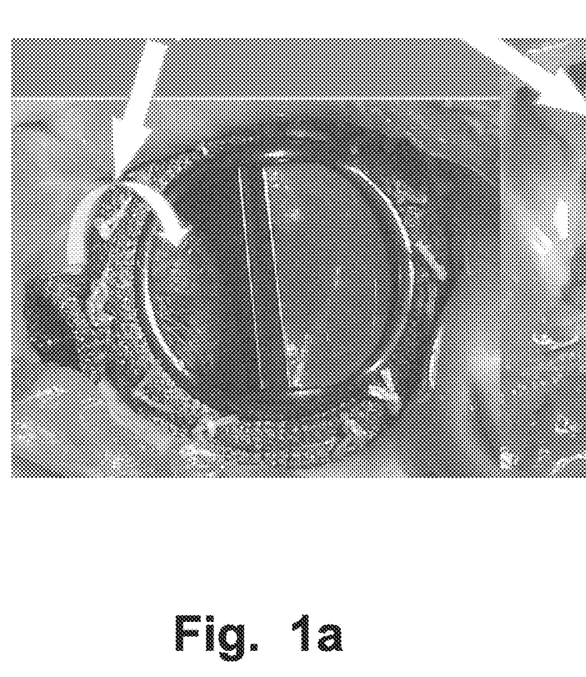
FIGS. 1a-b shows a medical implantable occlusion device according to prior art.
Figure 1B:
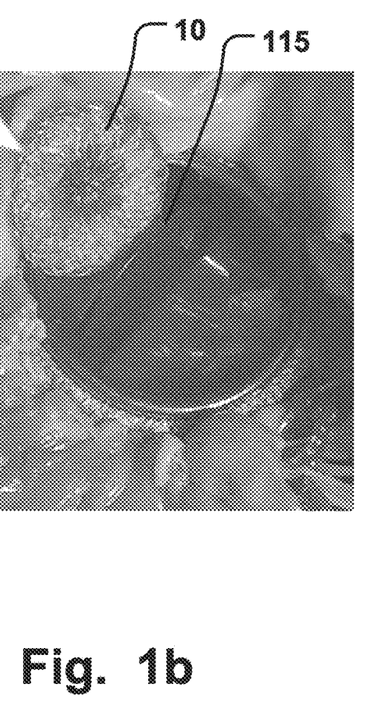

Occlusion devices exist that are used for treating PVL. FIGS. 1a-b shows such occlusion device when positioned at the periphery of the prosthetic valve from an atrial view (FIG. 1a) and from a ventricular view (FIG. 1b). The occlusion device has portions positioned on either side of the valve.

A problem with such previous occlusion devices is the disruption of the blood flow they create. Disruption of the blood flow is increasing risks for the patient for other complications and is detrimental to patient safety. The disruption can cause turbulence in the blood flow, which could increase the risks of embolies.

A further problem is the insufficient sealing that previous occlusion devices provide. Insufficient sealing may lead to further reoperations and unnecessary complications for the patient.

Another problem with the previous occlusion devices is the inability to adapt to the irregular and varying anatomy of the implantation site. Conformation to varying anatomies is critical for secure deployment of the occlusion device, without having to risk dislodgement and/or insufficient sealing.

A further problem with previous devices is problems with orientation and delivery of the device. Proper orientation is important for achieving the correct function of the device, and also for ease of the procedure.

All aforementioned problems affect not only patient safety but also available resources in the health care system as each patient will take longer to treat. Patient risks of previous paravalvular leak closure devices and methods include embolization of the device, stroke, arythmia, perforation of the biological prosthetic valve, and dysfunction of the valve prosthesis.

WO2008153872 discloses a device to be positioned on either side of the wall of a tubular blood vessel. Arcuate portions of the device conform to the tubular blood vessels surface.

Hence, an improved implant would be advantageous and in particular allowing for increased patient safety, flexibility, and/or cost-effectiveness would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device and a method according to the appended patent claims.

Embodiments of the present invention may be well suited for the selective occlusion of a vessel, lumen, channel, hole, cavity, or the like. One particular example, without limitation, of such a condition is Para-Valvular Leak (PVL). Another example is a vessel, lumen, channel, hole or shunt, through which blood flows from one vessel to another vessel such as an Atrial Septal Defect (ASD) or a Ventricular Septal Defect (herein after VSD), or Patent Ductus Arteriosus (PDA). Other examples could be an Arterial Venous Fistula (AVF), Arterial Venous Malformation (AVM), a Patent Foramen Ovale (PFO).

According to a first aspect of the invention a medical implantable occlusion device is provided comprising a fabric of at least one thread and a structural formation thereof having a collapsed and an expanded shape. The formation comprises a proximal and a distal portion, a longitudinal axis extending between the proximal and distal portion, and at least one of the proximal and distal portions comprises a peripheral edge having a first and a second radius of curvature in a direction substantially perpendicular to the longitudinal axis, and the first radius of curvature is different from the second radius of curvature.

According to a second aspect of the invention a medical method of occluding an opening such as a PVL is provided, comprising providing a device according to the first aspect of the invention, inserting the device in a collapsed state into the opening, expanding and releasing the device in the opening, thus anchoring the device in the opening for occluding the latter by the device.

Further embodiments of the invention are defined in the dependent claims, wherein features for the second and subsequent aspects of the invention are as for the first aspect mutatis mutandis.

Some embodiments of the invention provide for unrestricted blood flow through a prosthetic or native heart valve.

Some embodiments of the invention provide for flexible positioning of a medical implant to varying anatomical sites in a body of a human or animal.

Some embodiments of the invention also provide for secure attachment of a medical implant in a patient's vascular system.

Some embodiments of the invention provide for a medical implant that can be safely delivered and oriented at treatment site in a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a Para-Valvular Leak device (PLD). However, it will be appreciated that the invention is not limited to this application but may be applied to any other purposes of cardiac or vascular occlusion, and many other medical implantable devices, including for example filters, stents, Left Atrial Appendage (LAA) occluders, aneurysm treatment devices, grafts, etc.

Figure 3A:
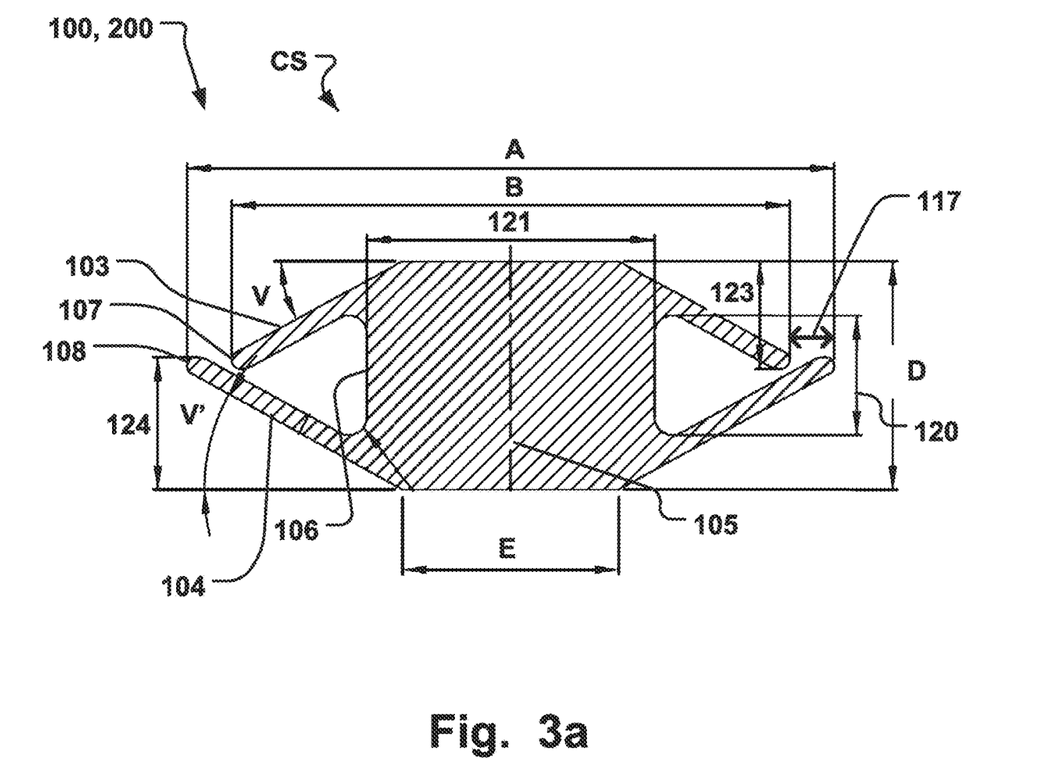
FIGS. 3a-c are side views along cross-section a (CS) of the medical implantable occlusion device in FIG. 2.
Figure 3B:
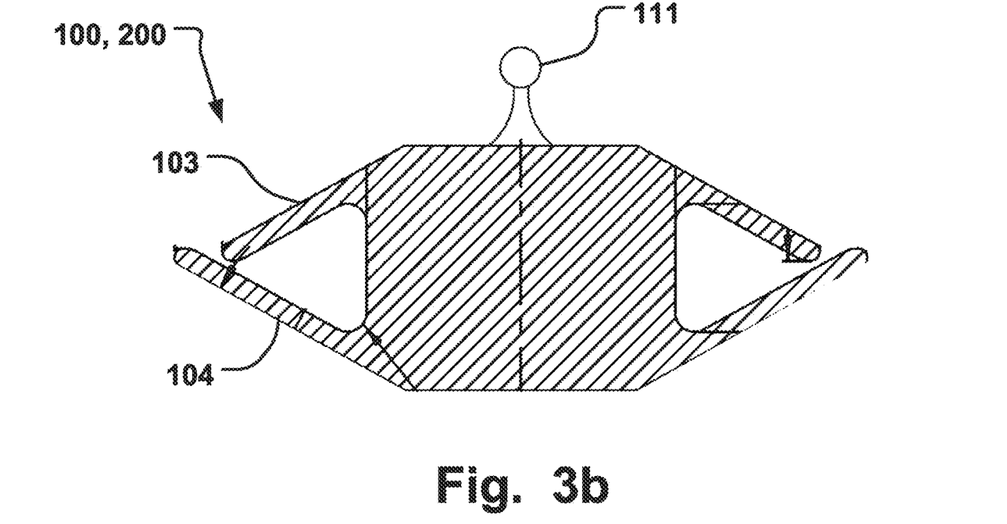
Figure 3C:
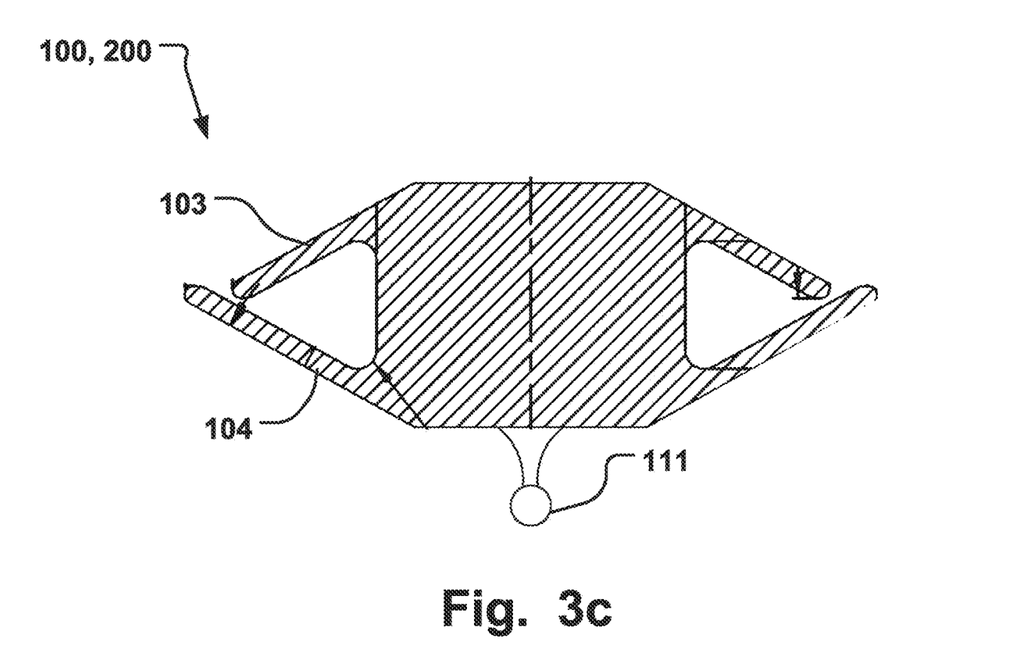
Figure 4:
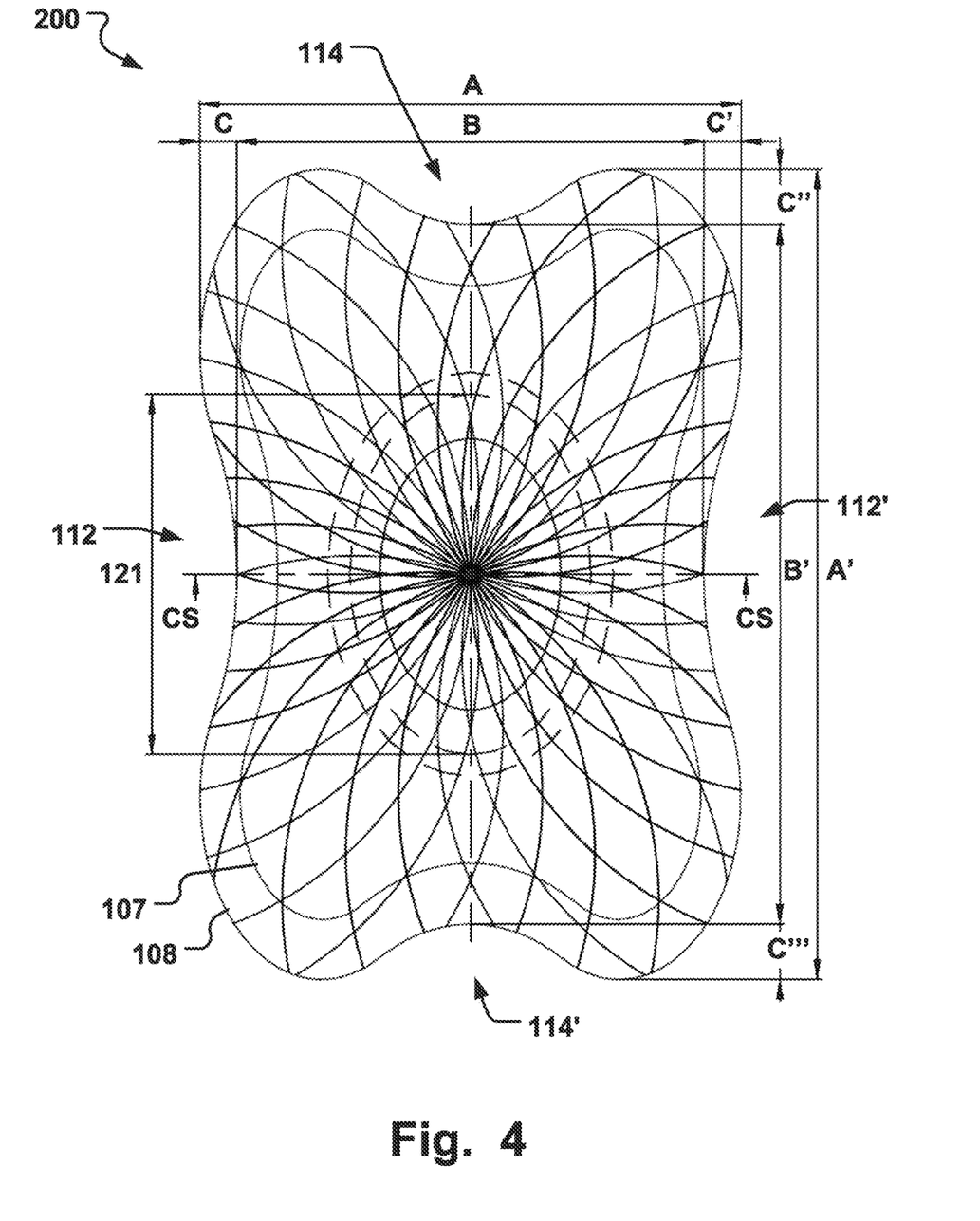
FIG. 4 is an illustration of a medical implantable occlusion device according to an embodiment of the invention.

FIG. 1 shows a medical implantable occlusion device 100 according to an embodiment of the invention. FIG. 4 shows a device 200 in another embodiment of the invention, which is similar to the device 100 in FIG. 1 but with other relative dimensions. The device 100, 200, comprises a fabric, mesh or braiding of at least one thread 101. The fabric may be formed from one thread or several. FIGS. 3a-c are cross-sections of the device 100, 200, along the line CS in FIG. 1 or FIG. 4, which will be discussed in further detail below.

Figure 2:
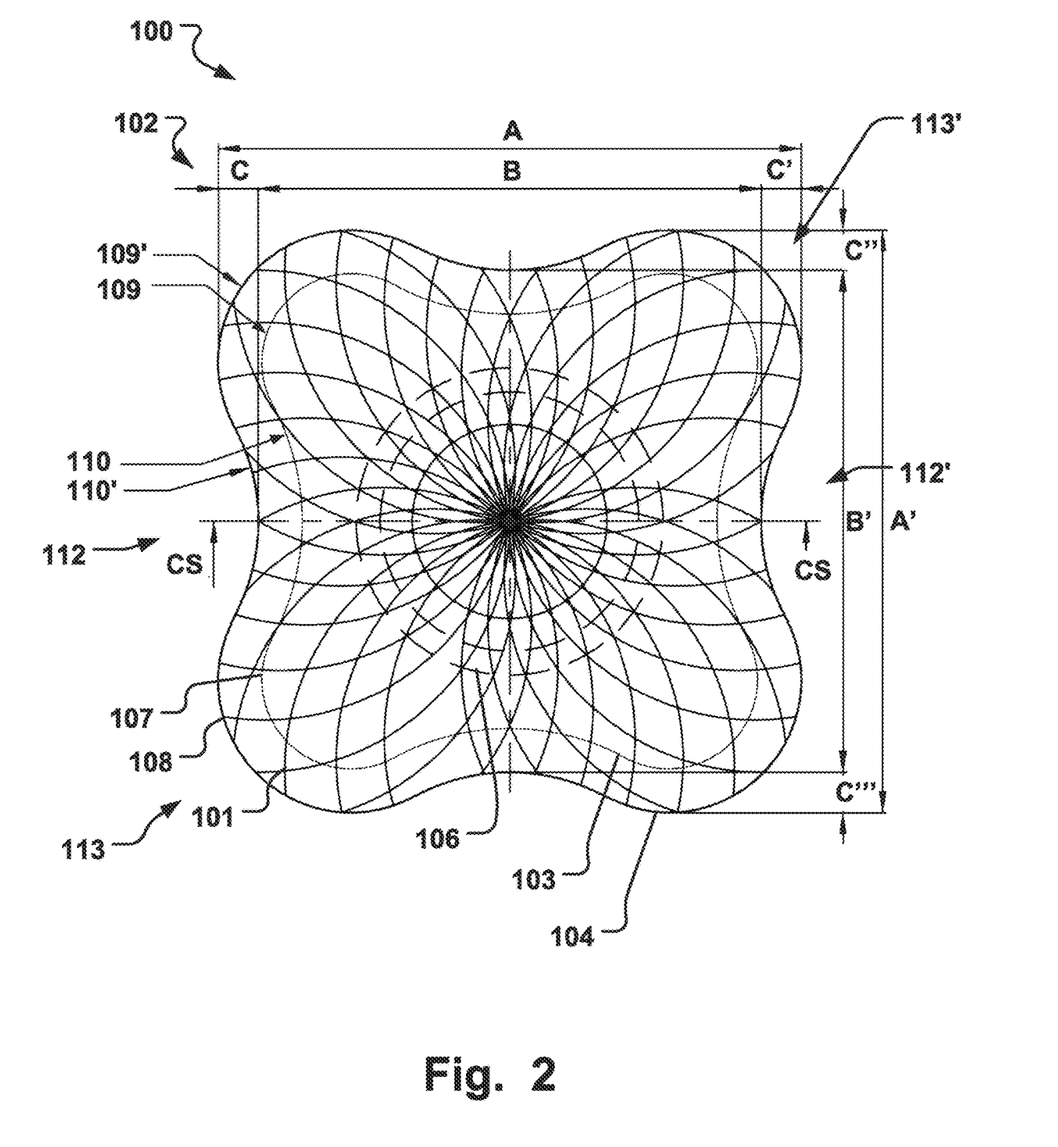
FIG. 2 is an illustration of a medical implantable occlusion device according to an embodiment of the invention.

The device 100, 200, or more particularly the structural formation 102 of the fabric of threads 101, has an unloaded expanded shape and a collapsed shape. Thus, in the expanded shape, wherein the device 100 has a shape as depicted in FIG. 1 and FIG. 2, no external force acts on the device 100, 200. The device 100, 200, may be stretched and thereby exhibit a smaller cross-section, in order to fit inside a delivery device such as a catheter. The device 100, 200, may be self-expandable between the collapsed shape and the expanded shape, i.e. when the device 100, 200, is removed from the confinement of the catheter the cross-section of the device 100, 200, returns to its originally defined value in the unloaded expanded shape. The device may be self-expandable due to an inherent elasticity of the threads in the fabric or braiding. The device may also have a shape memory, e.g. triggerable to go to the expanded shape at a switching temperature, such as body temperature.

The shape of the device 100, 200, in the expanded shape may be defined in a heat treatment procedure of the device 100, 200, or more particularly of the braiding of the device.

The dimensions of the device 100, 200, in the expanded, relaxed, shape are defined in the heat treatment procedure of the braiding.

The entire device 100, 200, may be comprised of a single, continuous fabric or braiding. The braiding may be made of a material suitable for implanting in a human or animal body, and suitable for being formed in a heat treatment procedure to a desired shape in the expanded shape and also in the stretched state. For example NiTinol may be used as a material for the device 100, 200. However, suitable materials for embodiments of the braiding are various and include shape memory materials, metal, superelastic alloys (such as NiTinol), or polymers, such as degradable polymers.

The structural formation 102 of the device 100, 200, comprises a proximal portion 103, and a distal portion 104. A longitudinal axis 105 extends between the proximal and the distal portion, which is best illustrated in FIG. 3a. In FIG. 3a it is also seen that the proximal, and distal portions 103, 104, may comprise expanded diameter portions 103, 104, that are separated by a waist 106 of reduced cross-section between the proximal and distal portions 103, 104. The length 120 of the waist 106 may correspond substantially to the wall thickness of the defect to be occluded, when the proximal and distal portions 103, 104, are positioned on either side of such defect. The flexible nature of the at least one thread 101 of the device 100, 200, however allows the device to adapt to a wide range defect dimensions. The proximal and distal portions 103, 104, will strive in a direction towards each other to the expanded shape when separated by the defect, thereby closing against the walls on either side of the defect and providing the occluding effect. The width 121 of the waist 106 may approximate the width of the defect, i.e. the width of the opening of the paravalvular leak defect.

Figure 10A:
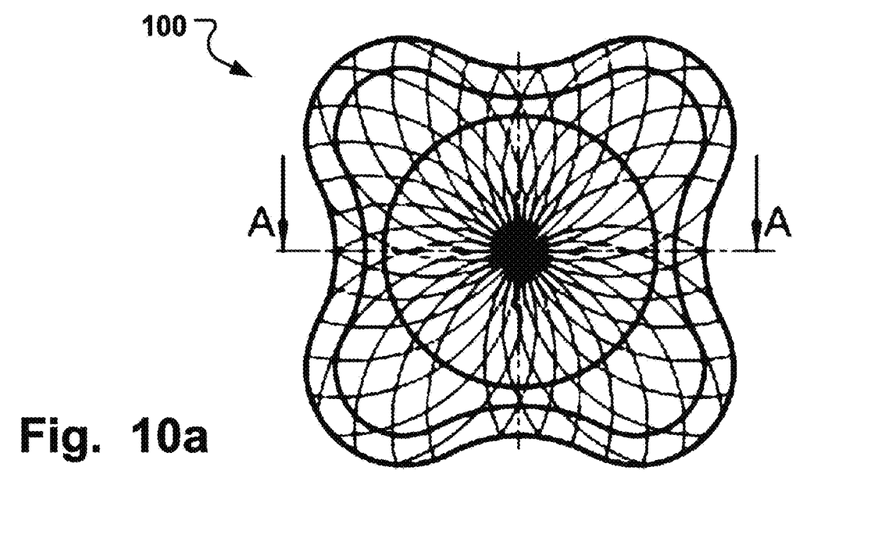
FIGS. 10a-c are illustrations of a medical implantable occlusion device according to an embodiment of the invention, shown in top-down view (a), and side views (b)-(c), respectively.
Figure 10B:
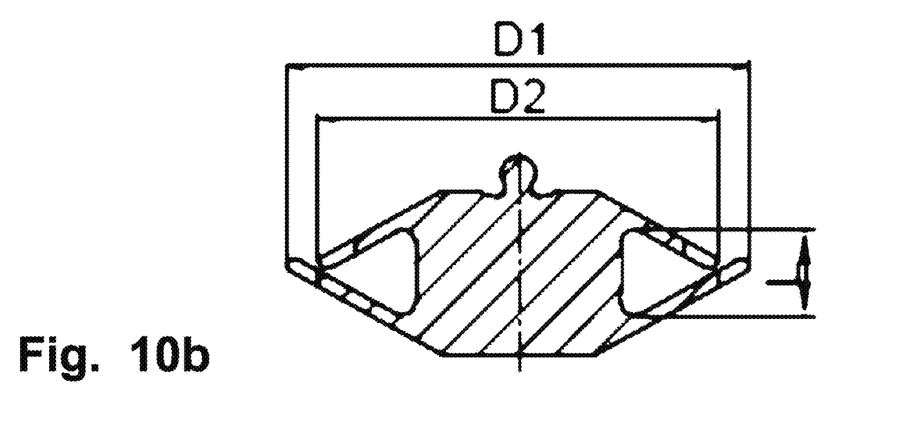
Figure 10C:
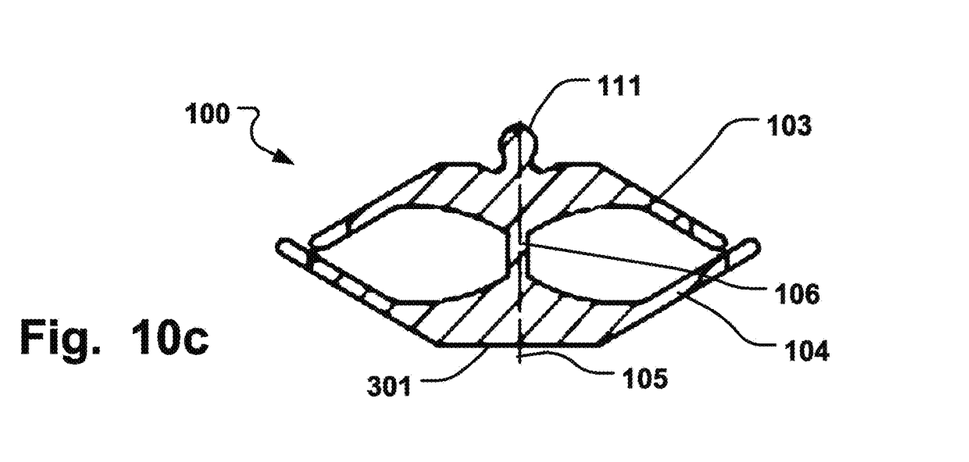

FIGS. 10b and 10c show two different types of waists 106, along the cross-section A of the device 100 seen in a top-down view in FIG. 10a. According to one embodiment the waist may comprise narrowly or tightly twisted threads 101, of the fabric or braiding of the device 100, around the longitudinal axis 105, in order to produce a waist 106 of small cross-section relative to the diameter of the proximal and distal portions 103, 104. This small cross-section allows for fitting of the device in small openings to be occluded. During manufacturing of the device 100, the proximal and distal portions 103, 104, may be twisted in relation to each other around the longitudinal axis 105, during a heat setting step, to produce a waist 106 with twisted threads 101. This may be part of a subsequent heat setting step, after a first heat setting step for forming the expanded diameter portions, i.e. the proximal and distal portions 103, 104, and the reduced diameter portion, i.e. the waist. Alternatively, the twisting is made during the same first heat setting step.

The waist 106 may be made of a portion of parallel threads or a more densely braided section of the fabric at the waist 106, providing for particular strength in the longitudinal direction. The waist 106 may be arranged concentrically with respect to the proximal and distal portions 103, 104, but an asymmetric configuration may be suitable in particular anatomies to be occluded.

At least one of the proximal and distal portions 103, 104, comprises a peripheral edge 107, 108, having a first 109, 109', and a second 110, 110', radius of curvature in a direction substantially perpendicular to the longitudinal axis 105. The first radius of curvature 109, 109', is different from the second radius of curvature 110, 110'. In this way the peripheral edge 107, 108, may conform to various anatomical geometries neighboring the defect to be occluded, hence avoiding unnecessary blockage and disruption of e.g. blood flow, while still providing the occlusion of the defect.

Figure 6:
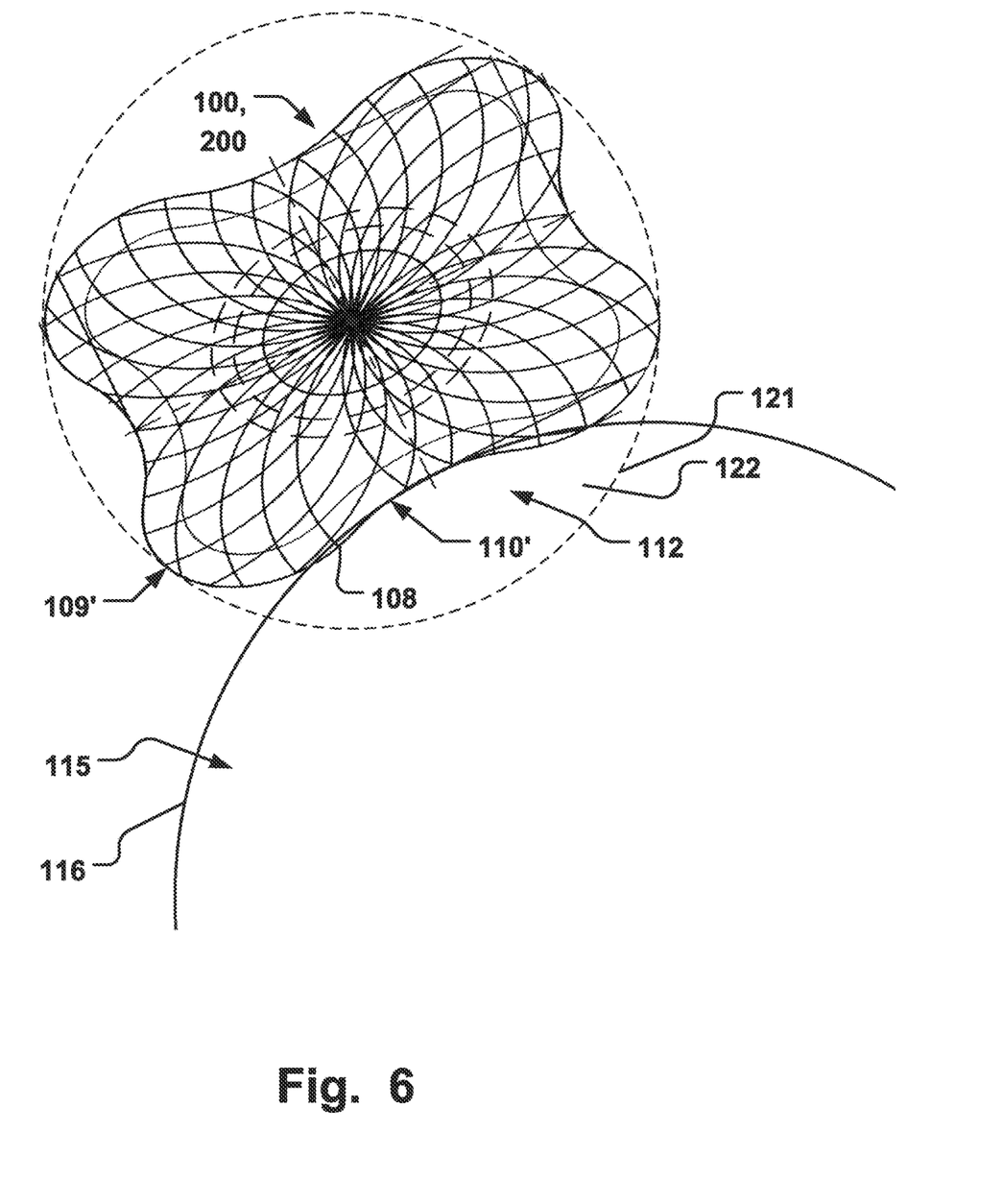
FIG. 6 is an illustration of a medical implantable occlusion device according to an embodiment of the invention when implanted at a treatment site.

In case of paravalvular leak defects (PVL) the at least one of the first and second radius of curvatures may be chosen such that the curvature of at least a section of the peripheral edge 107, 108, corresponds substantially to a valve curvature 116 of a valve 115 for regulating blood flow. This is illustrated in FIG. 6, where the device 200 occludes a PVL close to the outer boundary of the valve 116. The device 200 has a peripheral edge 108 with a second radius of curvature 110' that corresponds substantially to the valve curvature 115. The first radius of curvature 109' as exemplified in FIG. 6 is different from the second radius of curvature 110' of the peripheral edge 108, and the peripheral edge 108 may have any shape to conform to varying neighboring geometries where the influence of the occlusion device must be minimized while providing the necessary occlusion effect.

Figure 5A:
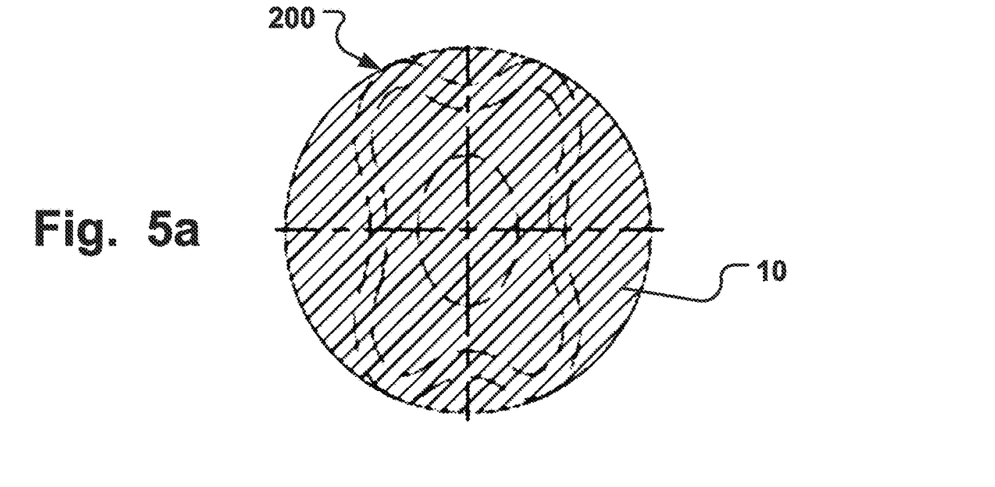
FIGS. 5a-c are illustrations of a medical implantable occlusion device according to an embodiment of the invention.
Figure 5B:
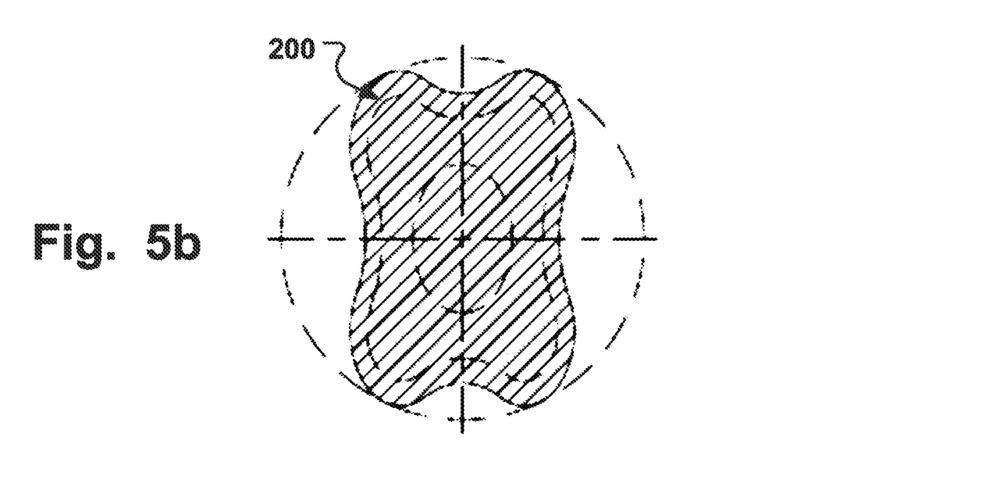
Figure 5C:
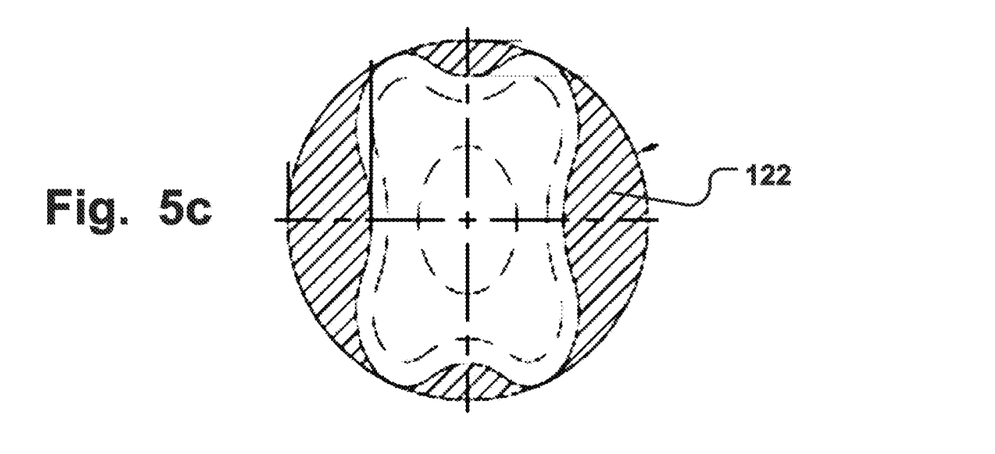

A prior art device 10 is shown in FIGS. 1a-b, which is a typical example of the influence such prior art devices have on the prosthetic valve because of its substantial blockage of the valve 115 when positioned in a PVL at the periphery of the valve 20. FIG. 1a is a view from the atrial side, and FIG. 1b is a view from the ventricular side, where the latter most clearly shows the device 10 extending over a substantial portion of the valve 20. Such device 10 may disrupt the blood flow, create turbulence and lead to various complications as discussed above. Returning to FIG. 6, the corresponding overreach across the valve 115 resulting from such prior art devices is marked with dashed line 121. The varying radius of curvature 109', 110', of the device 100, 200, allows occlusion of PVL close to the valve 115 without any overreach across the valve and the associated complications. FIGS. 5a-c illustrates the amount of area that is saved by the device 100, 200, which otherwise would have negative impact. FIG. 5a shows the coverage by a prior art device 10 (dashed lines), and FIG. 5b shows the coverage by the device 200, while FIG. 5c shows the differential area 122 that is saved which will not block the flow of blood through the valve 115.

Both the proximal and distal portions 103, 104, may have peripheral edges 107, 108, with varying radius of curvature. FIG. 2 shows the first and second radius of curvature 109, 110, for the proximal portion 103, and the first and second radius of curvature 109', 110', of the distal portion 104 for the device 100. FIGS. 4 and 6 shows a similar configuration for the device 200. In this way the blood flow will not be disrupted on any side of the valve 115.

The dimensions of the device 100, 200, such as indicated in FIGS. 2 and 3, c.f. A, A', B, B', C, C', C", C'", D, E, may be adapted such that proper alignment of the device 100, 200, to the valve curvature 116 is achieved.

As seen in FIGS. 2, 4, 5, 6, the peripheral edge 107, 108, is concave radially outwards. I.e. in a direction substantially perpendicular to the longitudinal axis 105, FIG. 3a. This allows the peripheral edge 107, 108, to follow the convex shape of the valve curvature 116, so that no overlapping of the valve 115 occurs. The radius of curvature of the concave part can be varied as desired in order to achieve the closest correspondence with the valve curvature 116. The number of concave sections of the peripheral edge 107, 108, may vary. The devices 100, 200, in FIGS. 2, 4, 5, 6, have four concave sections, but it could be one, two, three, five or more. Leaks can occur around the valve 115 at a 360 deg location. The curvature of the peripheral edge 107, 108, may be sized and shaped to cover several PVL's around the valve curvature 116. Due to the varying radius of curvature or the concave peripheral edge 107, 108, several PVL's may be occluded with a single device 100, 200, without extending across the valve 115 and disturbing the blood flow.

As further shown, e.g. in FIG. 2, the peripheral edge 107, 108, comprises edge sections 112, 112', 113, 113', that are alternatingly concave and convex radially outwards in a direction substantially perpendicular to the longitudinal axis 105. Each of the concave edge sections 112, 112', also seen in FIG. 4 and denoted 114, 114', may be positioned against the valve curvature 116. The devices 100, 200, have the convex sections 113, 113', positioned in between the concave sections 112, 112', which results from having a several concave sections.

The geometric terms concave and convex as used herein is to be interpreted for the purposes of the invention as their normal geometrical meaning including any recesses in the device for the purpose of the term concave and protrusions of the device for the purposes of the term convex, where such recesses and protrusions may also define the spatial extent of the device 100, 200, i.e. the peripheral edge 107, 108, such that the device 100, 200, may follow the valve curvature 116. The peripheral edge 107, 108, may be continuous without sharp interruptions, kinks or corners, as illustrated in the Figures, or comprise discontinuous sections.

The device 100, 200, has radially opposed edge sections 112, 112', 114, 114', of the peripheral edge 107, 108, that have substantially the same radius of curvature, e.g. as seen in FIGS. 2 and 4. Such symmetry may provide ease of positioning against the valve curvature 116. In FIG. 2, the device 100, has substantially the same radius of curvature for all concave sections of the peripheral edge 107, 108. Alternatively, the device 100, 200, may comprise concave edge sections having different radius of curvatures 109, 109', 110, 110', which allows the device 100, 200, to conform to a wide range of valves 115, having different valve curvatures 116.

FIG. 4 shows a device 200 having first radially opposed edge sections 112, 112', of the peripheral edge 107, 108, having a radius of curvature that is larger than the radius of curvature of second radially opposed edge sections 114, 114'. As mentioned above this may provide selectivity to various geometries of the valve 115. By simply rotating the device 200, the physician may select one peripheral edge with a particular radius of curvature that conforms best to the valve curvature 116, and/or the opening to be occluded. Also, the device 200 may provide increased holding strength against the defect to be occluded by its increased radial extent along a first axis, while maintaining the limited radial extent along a second axis, being perpendicular to the first axis, i.e. the second axis extending in direction across the valve 115. Overlap across the valve 115 by the device 200 (along the aforementioned second axis) is thereby avoided, while increased holding strength is provided.

The peripheral edge may comprise at least two edge sections 112, 112', or 114, 114', that are concave radially outwards in a direction substantially perpendicular to said longitudinal axis. Having more than one concave edge may allow selectivity as described above, and/or ease of positioning if the edges have similar radius of curvature.

Further, by having a rotational symmetric device 100, 200, around axis 105, the ease of handling and insertion, and also stability and structural integrity of the device can be increased. This can be realized by having two radially opposed concave edges as described above. The radius of curvature of the peripheral edge 107, 108, may correspond to a particular defect to be occluded and/or the curvature of the valve.

The device 100, 200, may have a peripheral edge 107, 108, that defines a generally rectangular shape of the proximal or distal portion 103, 104. As seen in FIGS. 2 and 4, the device 100, 200, has four convex corners, see e.g. edge sections 113, 113', and concave sections in between, 112, 112'. The peripheral edge 107, 108, may have a radius of curvature that vary considerably, e.g. the convex corners 113, 113', of the device 100, 200, may be in the form of a sharp transition from one concave edge section to the next, as alternative to a smooth continuous transition. In either case the device 100, 200, may be referred to as having a generally rectangular shape due to having four corners in the Figs. As mentioned above the number of concave sections 112, 112', and corners, i.e. convex sections 113, 113' may vary, and the device 100, 200, may have generally triangular, pentagonal shapes etc, as long as the peripheral edge 107, 108, has at least a section of its curvature that can be positioned close to the valve curvature 116 without extending across the valve 115, when the device 100, 200, is in its implanted site.

At least one of the proximal and distal portions 103, 104, may be deflected towards the other portion with an angle V, V'. In this way the device 100, 200, may better accommodate to the anatomy at the implanted site and thereby provide a closer fit against the tissue by the proximal and/or distal portion 103, 104, for improved occlusion. For example, at the periphery of the valve 115, there is often a "volcano crest", i.e. a protrusion going around the periphery. When the proximal or distal portion 103, 104, is positioned close to that protrusion the deflection of the aforementioned portions towards each other with angle, V, V', allows these portions to reach over the protrusion and down to the tissue nest to the protrusion for a secure fit. FIG. 3a shows the cross-section of the device 100, 200, where the proximal portion 103 is deflected towards the distal portion 104 with an angle V, and the distal portion 104 is deflected towards the proximal portion 103 with an angle V'. The angles V and V' may be substantially the same or different depending on the anatomy of the site in the vascular system to be occluded. E.g. the distances 123, 124, as indicated in FIG. 3a, may be varied. Only one of the portions 103, 104, may be angled towards the other. The device 100, 200, may thereby be adapted to the irregular and varying anatomy of the implantation site. This also allows for a particular stable long-term construction even in anatomical situations where a continuous movement at the implantation site is present.

One of the proximal and distal portions 103, 104, may have a larger diameter than the other portion, thereby creating an overlap 117 between the proximal and distal portions 103, 104. The overlap may provide increased sealing ability of the device 100, 200, e.g. when the portions 103, 104, being pressed towards each other. The overlap may substantially be in the radial direction, perpendicular to longitudinal axis 105. As seen in FIG. 3a, the distal portion 104 overlaps the proximal portion 103 in the radial direction, which is also seen in e.g. FIG. 2 with respect to peripheral edges 107, 108. When the distal portion 104 is placed on the side of the defect being exposed to high pressure, e.g. on the ventricular side of the heart (depending on which valve that has PVL; Aortic, Mitral, Tricuspid, or Pulmonary), the larger area of the distal portion 104 will improve the sealing against the tissue, while the smaller area of the proximal portion minimizes overlap across the valve 115. Thus a secure occlusion is achieved even before the device 100, 200, is securely covered with endothelia and tissue integrated with the surrounding tissue.

The diameter may be equivalent to the largest cross-section throughout the disclosure.

The proximal and distal portions 103, 104, may be substantially flat and having a diameter larger than the opening of the PVL which it is placed.

Figure 7A:
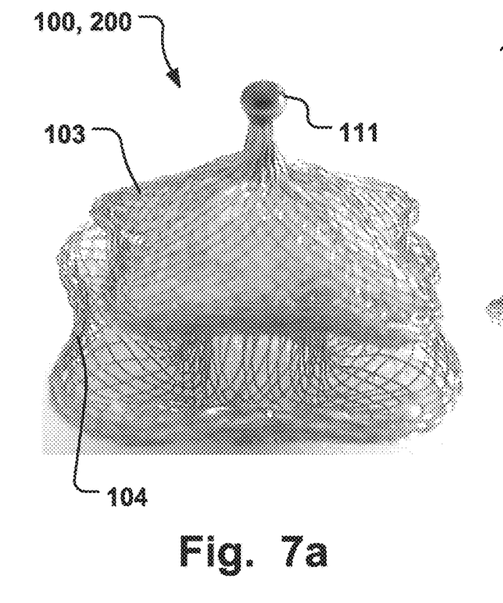
FIGS. 7a-d are illustrations of a medical implantable occlusion device according to an embodiment of the invention.
Figure 7B:
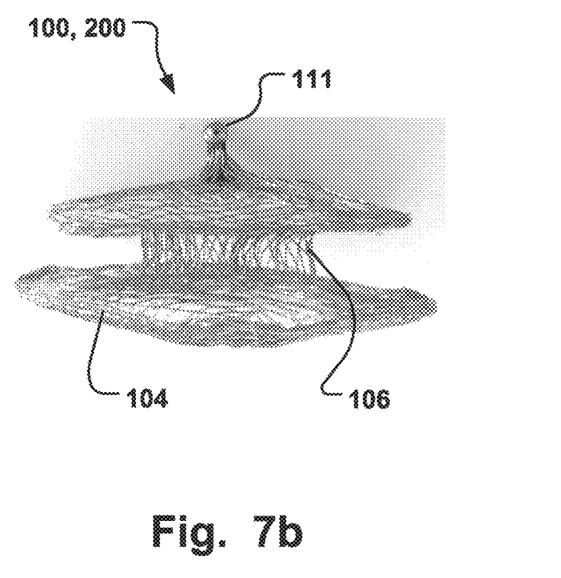
Figure 7C:
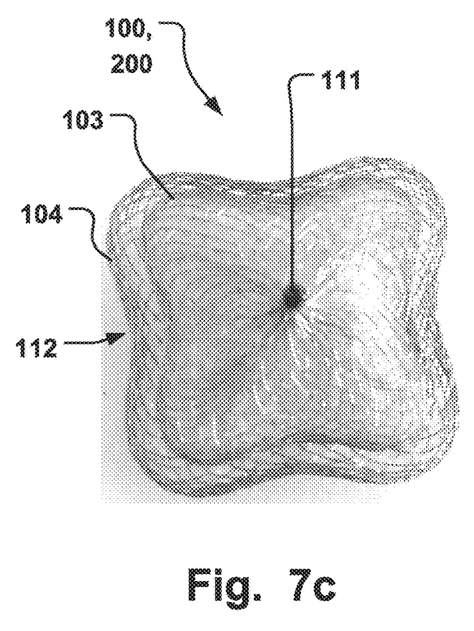
Figure 7D:
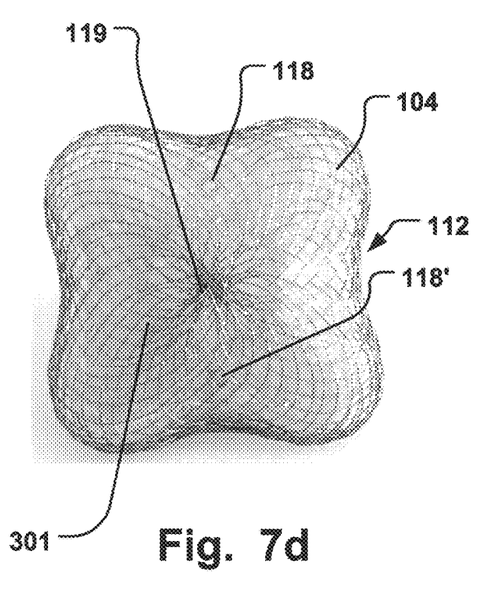
Figure 8:
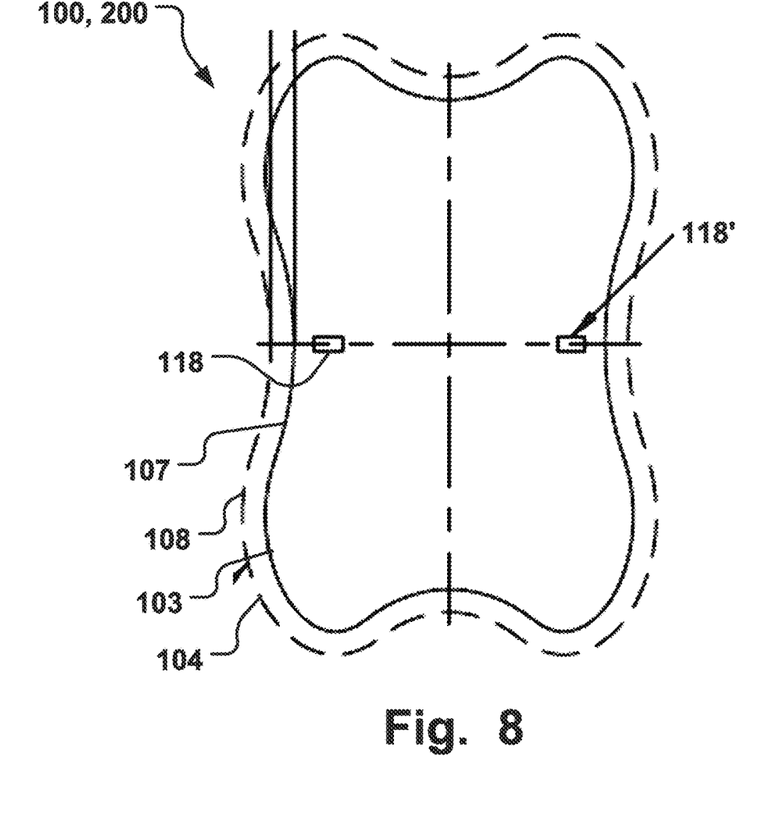
FIG. 8 is an illustration of a medical implantable occlusion device according to an embodiment of the invention.

FIGS. 7a-d shows perspective view of the device 100, 200, i.e. FIG. 7a is a tilted side view, FIG. 7b is a side view, FIG. 7c is a top-down view facing the proximal portion 103, and FIG. 7d is a top-down view facing the distal portion 104. Even though the device in FIGS. 7a-d more closely reassembles the device 100 in FIG. 2 due to having substantially sides of equal length, the perspective views in the Figs. is also representative of the device 200 in FIG. 4. The device 100, 200, may comprise at least one a marker element 118, 118', for aiding in orienting the device 100, 200. Such marker 118, 118', allows identification of the device and reassurance that the device has been implanted correctly. For example, it can be determined whether the concave edge section 112 of the peripheral edge 107, 108, has been aligned against the valve curvature 116. Thus, the at least one marker element 118, 118', may be arranged on one of the proximal and distal portions 103, 104, at a position corresponding substantially to the location of the peripheral edge 107, 108. FIG. 8 illustrates the location of two markers 118, 118', which are close to the peripheral edge 107 of the proximal portion 103. The markers 118, 118', may be arranged on opposite concave sections, as illustrated in the figure for allowing correct positioning. The markers 118, 118', may be attached to the proximal portion 103, or to the distal portion 104. Hence, the markers 118, 118', in FIG. 8 could be attached to the distal portion 104, for marking out the position of the peripheral edge 107 of the proximal portion 103. As the distal portion 104 may have increased diameter or circumference, the markers 118, 118', could be attached to the distal portion 104 at a distance from the peripheral edge 108 of the distal portion 104, while still marking out the peripheral edge 107 of the proximal portion. This may allow for easier attachment of the markers 118, 118', to the device 100, 200, and less interference with the operation of the device 100, 200, as the markers do not have to be attached to the proximal peripheral edge 107, while still allowing exact positioning with respect to the valve curvature 116 with the proximal peripheral edge 107.

The marker element 118 may comprise a radiopaque material, hence being identifiable in X-ray, or comprise material for easy identification in MRI. The device 100, 200, may comprise two markers 118 as shown in FIG. 7d, arranged across the radial direction of the distal portion 104, and/or alternatively of the proximal portion 103. Any number of markers 118 may be used for identification. The markers 118 may be fixated to an occluding element such as a patch, fibers or the like comprising a biocompatible material (e.g. PET) for supporting the sealing of the blood flow through the device 100, 200, or fixed to the fabric of threads 101 of the device 100, 200, itself.

As shown in FIGS. 3b, 3c and FIGS. 7a-c, the device 100, 200, may comprise a connecting member 111 attached to one of the distal and proximal portions 103, 104, for connection to a delivery device (not shown). The delivery device may grasp the connection member 111 which may be spherical in shape, thus providing a pivoting motion of the device 100, 200, in relation to the delivery device in combination with secure attachment. The connection member 111 may be arranged on the proximal portion 103 as shown in FIG. 3b, or on the distal portion 104 as shown in FIG. 3c. FIG. 7a-c illustrates the device 100, 200, having the connection member 111 on the proximal portion 103. In reality the portion having the connection member 111 becomes the proximal portion in use of the device, but the above conventions are used for conciseness in the description and figures. Hence, the connection member 111 may be arranged on the expanded diameter portion 104, or the increased diameter portion 104. This allows the possibility to access the PVL from both sides of the leak.

The connecting member 111 may be configured for connection to a delivery device in a predetermined orientation. Hence a specific orientation of the device 100, 200, could be maintained relative to the delivery device during implantation which may aid in positioning the device 100, 200, in relation to the valve curvature 116.

The ends of the at least one thread 101 forming the fabric may be fixed to the connecting member 111. The connecting member 111 may thus be a weld or any other attachment means for the threads 101 of the fabric. The distal portion 104 may comprise returning loops 119 of the at least one thread 101, meaning that opposite ends of the at least one thread 101 forming the distal portion 104 are fixed to the connecting member 111. By having returning loops only one collection point for the ends of the at least one thread 101 is needed. The connection member 111 may thus serve as a connection for these ends, thereby avoiding multiple connection points such as welds on the distal portion 104. Hence, a flat distal portion 104 may be provided, that increases the compactness of the device 100, 200. The flat distal portion 104 may thus be a closed continuous distal wall 301 of the braiding forming the device 100, 200, i.e. free from a thread ends. This reduces the risk thromboembolic complications. E.g. nothing is protruding into the blood stream, and there are no discontinuities that may cause thromboembolic complications. Further, due to the connection member 111 on the proximal end 103, the device 100, 200, may be delivered through the vena cava with improved safety to the patient. The implantation techniques are different for each PVL according to the valve and the location of the leak. Delivery to the high pressure arterial side of the vascular system is avoided, which provides for less complications and a medical procedure which is simpler to perform.

Figure 9:
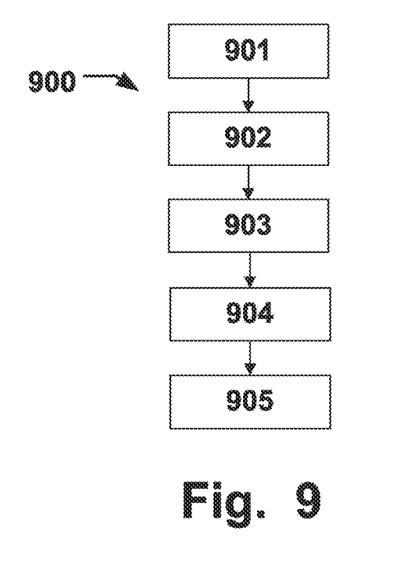
FIG. 9 is a flow chart illustrating a method of occluding a PVL in a body lumen with a medical implantable occlusion device according to an embodiment of the invention.

FIG. 9 illustrates a medical method 900 of occluding an opening in a body lumen, comprising providing 901 a device 100, 200, inserting 902 the device 100, 200 in a collapsed state into the opening, expanding 903 and releasing the device 100, 200, in the opening, thus anchoring 904 the device 100, 200, in the opening for occluding the latter by the device 100, 200. The opening may be a Para-Valvular Leak (PVL), and the method may comprise positioning 905, or rotating, the device 100, 200, such that a concave edge section 112, 112' of the device 100, 200, substantially follows the valve curvature 116 of the valve 115.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical implantable paravalvular leakage occlusion device for occlusion of paravalvular leakage at a heart valve, comprising:
    a braiding of at least one thread and a structural formation thereof having a collapsed and an expanded shape, said formation comprises
    a proximal and a distal portion,
    a longitudinal axis extending between said proximal and distal portion,
    wherein at least one of said proximal and distal portions comprises a peripheral edge that includes a plurality of rounded corners each having a corner radius smaller than a width of the occlusion device.

2. The occlusion device according to claim 1, wherein at least one of the first and the second edge section is configured to substantially follow a valve curvature of said valve when said device is expanded.

3. The occlusion device according to claim 2, wherein said proximal and said distal portions are nonplanar and curved, and a radius of curvature of said proximal portion is different than a radius of curvature of said distal portion.

4. The occlusion device according to claim 1, wherein said device is rotational rotationally symmetric around said longitudinal axis.

5. The occlusion device according to claim 1, wherein said peripheral edge comprises edge sections that are alternatingly inwardly curved and outwardly curved relative the longitudinal axis.

6. The occlusion device according to claim 1, wherein said peripheral edge comprises radially opposed edge sections having substantially the same radius of curvature relative the longitudinal axis.

7. The occlusion device according to claim 1, wherein one of said proximal and distal portion has a larger diameter than the other portion, and wherein an overlap between the proximal and distal portion is provided.

8. The occlusion device according to claim 7, wherein the proximal portion is deflected towards the distal portion with an angle, the distal portion is deflected towards the proximal portion with an angle, and wherein the distal portion overlaps the proximal portion in the radial direction of said device.

9. A medical implantable paravalvular leakage occlusion device for occlusion of paravalvular leakage at a heart valve, comprising:
    opposed distal and proximal braided members joined by a connecting member having a width that is smaller than widths of the distal and proximal braided members;
    wherein at least one of the distal and proximal braided members has a periphery that includes a plurality of rounded corners;
    wherein at least one of the plurality of rounded corners has a radius with a center that is spaced apart from a center of said connecting member.

10. The occlusion device according to claim 9, wherein at least one of the first and the distal and proximal braided members is shaped to substantially follow a valve curvature of a heart valve.

11. The occlusion device according to claim 9, wherein said proximal and said distal portions are nonplanar and curved, and a radius of curvature of said proximal portion is different than a radius of curvature of said distal portion.

12. The occlusion device according to claim 9, wherein said device is rotationally symmetric around said longitudinal axis.

13. The occlusion device according to claim 9, wherein said peripheral edge comprises edge sections that are alternatingly inwardly curved and outwardly curved relative the longitudinal axis.

14. The occlusion device according to claim 9, wherein one of said proximal and distal portion has a larger diameter than the other portion, and wherein an overlap between the proximal and distal portion is provided.

15. The occlusion device according to claim 14, wherein the proximal portion is deflected towards the distal portion with an angle, the distal portion is deflected towards the proximal portion with an angle, and wherein the distal portion overlaps the proximal portion in the radial direction of said device.

16. A medical implantable paravalvular leakage occlusion device for occlusion of paravalvular leakage at a heart valve, comprising:
    opposed distal and proximal braided members joined by a connecting member having a width that is smaller than widths of the distal and proximal braided members;
    wherein at least one of the distal and proximal braided members has a periphery that includes a plurality of inflection points; wherein said inflection points are created by rounded corners, at least one of which having a radius that has a center that is spaced apart from a center of said connecting member.

17. The occlusion device according to claim 16, wherein said connecting member comprises a waist.

18. The occlusion device according to claim 16, wherein said device is rotationally symmetric around said longitudinal axis.

19. The occlusion device according to claim 16, wherein said connecting member comprises a twist.

* * * * *